United States Patent [19]

Kondo

[11] Patent Number: 4,631,174
[45] Date of Patent: Dec. 23, 1986

[54] MULTILAYER CHEMICAL ANALYSIS MEMBER HAVING AN OUTER WATERPROOF LAYER

[75] Inventor: Asaji Kondo, Saitama, Japan

[73] Assignee: Fuji Photo Film Co., Ltd., Kanagawa, Japan

[21] Appl. No.: 718,976

[22] Filed: Apr. 2, 1985

Related U.S. Application Data

[63] Continuation-in-part of Ser. No. 614,590, May 29, 1984, abandoned, which is a continuation of Ser. No. 177,553, Aug. 13, 1980, abandoned, which is a continuation of Ser. No. 35,182, May 2, 1979, abandoned.

[30] Foreign Application Priority Data

May 2, 1978 [JP]   Japan ................................. 53-59888

[51] Int. Cl.$^4$ ............................................. G01N 33/52

[52] U.S. Cl. ...................................... 422/56; 435/805; 436/810

[58] Field of Search ..................... 435/805; 436/810; 422/56

[56] References Cited

U.S. PATENT DOCUMENTS 3,554,871 1/1971 Lariccia ........................... 435/805 X
4,042,335 8/1977 Clement .................................. 422/56

Primary Examiner—Sidney Marantz
Attorney, Agent, or Firm—Sughrue, Mion, Zinn, Macpeak and Seas

[57] ABSTRACT

Chemical analysis sheets comprising a reagent layer, a porous spreading layer and a cover layer provided with a small opening are disclosed. The cover layer prevents rapid evaporation of moisture to ensure a complete reaction between the chemical reagent and the ingredient tested for.

9 Claims, 2 Drawing Figures

MULTILAYER CHEMICAL ANALYSIS MEMBER HAVING AN OUTER WATERPROOF LAYER

CROSS REFERENCE TO RELATED APPLICATIONS

This is a continuation of application Ser. No. 614,590, filed May 29, 1984, now abandoned, which is a continuation of application Ser. No. 177,553, filed Aug. 13, 1980, now abandoned which is in turn a continuation of application Ser. No. 35,182, filed May 2, 1979, now abandoned.

BACKGROUND OF THE INVENTION

1. Field of the Invention

This invention relates to sheet materials used for chemical analysis having a multilayer construction. In particular, the present invention relates to test sheets for analyzing blood serum, urine and other biological fluids.

2. Description of the Prior Art

Various types of multilayer sheet materials for chemical analysis are known. They include test sheets for spot analysis of samples in the form of aqueous solutions and, in particular, those of a multilayer construction suited for rapid and simple quantitative analysis and examination of ingredients involved in fluid samples from the living body such as blood, urine, etc. Such test sheets comprise a transparent substrate, one or more layers containing chemical reagents provided thereon and a porour spreading layer superimposed on the chemical reagent layer. These layers are firmly bonded to each other to form a unified structure. In some instances, the substrate may be eliminated.

U.S. Pat. No. 3,992,158 describes multilayer elements for qualitative and quantitative analysis of liquids such as blood serum and urine, which elements preferably comprise an isotropically porous spreading layer in fluid contact with a reagent layer which comprises at least one material interactive with a component or decomposition product of a component of the liquid.

U.S. Pat. No. 3,983,005 describes a multilayer element for analysis of cholesterols in a liquid such as serum. The element is of the type which comprises two superposed layers comprising a spreading layer in liquid contact with a reagent layer, and optionally, a support. Cholesterol oxidase and a cholesterol ester hydrolyzing composition comprising lipase having cholesterol estrase activity and protease are included in the reagent layer. Membrane filters or the like isotropically porous layers can be used as the spreading layer.

In addition, U.S. Pat. No. 4,042,335 describes multilayer elements for analysis of liquids, which comprise three superposed layers including a reagent layer, a radiation-blocking layer and a registration layer. U.S. Pat. No. 4,066,403 describes a multilayer analysis element comprising two reagents and a barrier composition separating the reagents. U.S. Pat. No. 4,050,898 describes a multilayer analysis element having therein a nonionic surfactant-containing spreading layer. U.S. Pat. No. 4,069,016 describes multilayer elements for analysis of a liquid to detect the bilirubin content in the liquid. U.S. Pat. No. 3,526,480 describes integral analysis elements adapted for automated test procedures.

When a drop of the sample fluid to be examined is applied to the spreading layer of such test sheets, diffusion of the fluid into the underlying reagent layer occurs concurrently with lateral spreading in the spreading layer, causing a chemical reaction to proceed upon contact with the chemical reagent in the reagent layer. Since a colored reaction product forms or discoloration takes place, one can quantitatively analyze the extent to which the reaction has proceeded by observing or examining the color of the reagent layer directly or through the substrate. For this purpose, color developing reactions caused by suitable organic reagents in an aqueous medium are particularly preferred. Such analysis self-evidently depends on the reaction between the ingredient tested for involved in the fluid sample and the chemical reagent contained in the reagent layer. Even comparatively rapid reactions take one minute or longer periods while slower reactions take from about 5 to 10 minutes as in the case of reactions relying upon enzymes as an active material at a temperature near 35° C. For instance, Example 3 of British Pat. No. 1,440,464 or French Pat. No. 2,191,734 is an example of an analysis sheet where the reaction time is short. In this Example, the reagent layer is composed of silver chromate and gelatin and upon reaction it turns from reddish brown to yellow due to chlorine ion present in the blood. Example 1 of U.S. Pat. No. 3,983,005 is an example where the reaction time is long. The reagent system used therein is composed of cholesterol oxidase, peroxidase and 4-methoxy-1-naphthol, and when free cholesterol is detected in the serum, the reaction continues over a period of time from about 5 to 20 minutes whereupon the color of the system becomes dark. Further, the existence of ample water is required until termination of the reaction.

To check the effect of the moisture present in the reaction environment in advance of the reaction, a sample fluid was dropped on two separate spots of an analysis sheet. In this case, the analysis sheet was a multilayer analysis element (or sheet) comprising in order a support, a reagent layer and a spreading layer. One of the spots was left open to the air while the other spot was covered with a thin film to prevent evaporation of the moisture after the applied fluid diffused into the spreading layer. In the former spot, the moisture evaporated rapidly thus suppressing the color developing reaction, whereas the latter covered spot remained moist for more than 20 minutes during which time the color developing reaction continued to completion. The above-described comparison indicates that the prevention of moisture escape from the sample fluid applied on the analysis sheet is essential for such a new type of multilayer analysis sheet to be acceptable in the market as a useful tool for simple and rapid quantitative analysis.

If one wants to prevent moisture evaporation from a conventional analysis sheet comprising only a spreading layer, a chemical reagent layer and a substrate, one must apply a cover to the test spot several seconds after the application of the fluid, i.e., after the fluid has diffused into the spreading layer.

Such fluid application followed by the application of a cover seriously conflicts with continuous or automated analysis using an analysis sheet.

SUMMARY OF THE INVENTION

A principal object of the present invention is to provide a chemical analysis or test sheet having a multilayer construction which does not dry out during analysis such that the reaction between the material tested for and the chemical reagent in the analysis sheet have an opportunity to fully react with one another.

Another object of the present invention is to provide a chemical analysis sheet to which the test sample may be applied with substantially little care and a circular pattern is invariably formed.

Still another object of the present invention is to provide a sheet which is easily handled prior to and during testing and which possesses excellent storage stability.

DETAILED DESCRIPTION OF THE INVENTION

Figure 1:
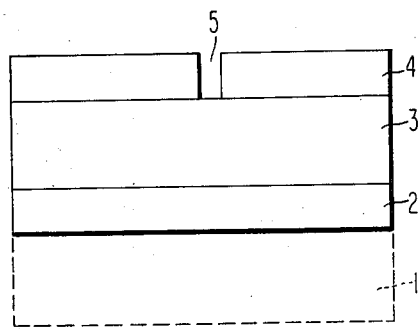
FIG. 1 is a cross-sectional view of the multilayered chemical analysis member of the instant invention.

The present invention has been devised to solve the problems involved with conventional multilayer chemical analysis sheets, and is characterized by a waterproof cover layer provided with a small opening overlying the porous spreading layer and a chemical reagent layer superposed in that order. Such a waterproof layer may be made from a metal foil (e.g., aluminum), cellophane, various types of paper including paraffin-impregnated paper, polymer laminated paper, water-resistant paper, etc., synthetic polymers such as polyethylene, polypropylene, poly(vinyl chloride), Saran resin (a trade name for vinylidene chloride/vinyl chloride copolymer), polycarbonate, polyester (e.g., poly(ethylene terephthalate)), cellulose ester (e.g., cellulose triacetate)), etc. One can still utilize other materials which are capable of preventing the penetration or evaporation of water. The surface of the materials cited above may further be treated with water repellent compounds such as an organopolysiloxane, a perfluoroalkyl compound, etc. A suitable thickness of the waterproof layer is about 8 microns to about 1 mm, and more preferably about 15 microns to about 0.5 mm.

The shape of the opening may be polygonal or circular, and its size can be from of pin-point (about 30 microns in diameter) to about 4 mm in diameter. For each test spot, only one opening is ordinarily required, however, two or more relatively small apertures may be provided with a diameter of from about 30 microns to about 0.5 mm. Such multiple openings may be located within a circle of about 1 mm to 5 mm in diameter. The shape of such an opening need not always be a hole but can simply be a cut like an asterisk, a cross or a linear slit.

In order to provide and fix the waterproof layer on the porous spreading layer, one may apply a coating solution to the spreading layer containing a waterproof layer forming material. A more preferable method, however, is to rely on adhesive bonding of an independently produced waterproof film. Suitable adhesives include those sensitive to pressure, heat or solvent or of a reactive type. Among these, pressure-sensitive adhesives are recommended since the processing operations are simple. When adhesive bonding, however, care must be taken that the adhesive does not impregnate too deep into the interior of the spreading layer. Also, those adhesives that are readily decomposed or attacked by water must be avoided. For practical manufacture commercially available pressure-sensitive adhesive tapes or sheets the backing of which comprises poly(ethylene terephthalate), poly(vinyl chloride), or regenerated cellulose can be employed. Such tapes are laminated on the spreading layer after having been appropriately perforated or processed.

Porous spreading layers may comprise, as set forth in the patent specifications previously cited, fibrous or nonfibrous materials, micro-porous membrane filter or polymer films filled with finely divided powder particles. Typical examples of fibrous materials which may be used are filter papers such as Schleicher & Schüll No. 2316 (see U.S. Pat. Nos. 3,802,842 and 3,552,928), Eaton-Dikeman No. 623 (see U.S. Pat. No. 3,699,003), Whatman 3MM (see U.S. Pat. No. 3,011,374), etc. Typical examples of non-fibrous materials which may be used are membrane filters such as Milipore MF Filter, Gelman Metricel GA-1 or 3, Fuji Film FM Filter, etc.

The chemical reagent layer comprises a chemical reagent included in a suitable hydrophilic or hydrophobic medium and capable of directly or indirectly reacting with the ingredient of concern contained in the sample fluid. Reagents which give rise to a colored reaction product or cause a distinct change in color are preferred. For example, a reagent layer for detecting glucose in the blood comprises glucose oxidase, peroxidase, o-dianisidine hydrochloride and gelatin as described in Example 1 of U.S. Pat. No. 3,992,158.

Suitable materials for the support include polyester, polycarbonate, cellulose ester and other optically transparent polymer films having a thickness of from about 10 microns to 0.5 mm. Another type of support comprises a releasable sheet such as a semi-transparent or opaque paper or tape treated with a releasing agent such as polysiloxane compounds. Such releasable sheets operate as a protective cover while attached to the chemical reagent layer and may be removed for subsequent measurements.

Though conventional multilayer chemical test sheets have generally been in a sheet form, the member of the instant invention can use supports of different forms such as a thick board or stick in addition to a sheet or film. Therefore, the multilayer chemical analysis member of the instant invention includes but is not limited to the conventionally known sheet-formed members. The most preferable structures for the members of the instant invention are the sheet and thin tape types.

Figure 2:
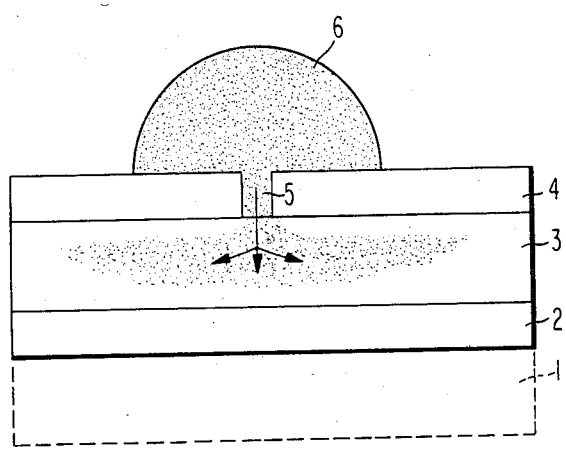
FIG. 2 illustrates application of the sample fluid into the porous spreading layer by diffusion; the arrows in the figure show the direction of diffusive flow of the fluid.

The multilayered chemical analysis member of the instant invention will now be explained more in detail with reference to the accompanying drawings, in which FIG. 1 is a cross-sectional view of the multilayer chemical analysis member of the instant invention. In the figure, 1 is a support or a releasable paper which may be adopted according to the use, 2 is a chemical reagent layer, 3 a porous spreading layer, 4 a waterproof layer, and 5 is a small opening. All of these layers are bonded together in a unified structure. FIG. 2 is a schematic diagram of the same member shown in FIG. 1 in operation in which a drop of sample fluid 6 is applied at the opening, and diffuses into the porous spreading layer. Like parts are designated using the same numeral as in FIG. 1. Gradually, the sample fluid diffuses into the chemical reagent layer and undergoes a color developing reaction as described above.

The advantageous features of the instant invention are summarized below.

(1) The supply and expansion of the sample fluid applied to the opening proceeds very smoothly into the porous spreading layer. At the same time, the fluid spreads laterally. No harmful secondary effects such as retardation of expansion caused by the presence of the waterproof surface layer are observed.

(2) Using the conventional type of analysis sheet, the operator must bring a drop of sample fluid grown at the tip of a pipette into contact with the spreading layer very carefull, otherwise, rough and careless application tended to result in an undesirable lateral flow of the fluid or in a spreading pattern deviating from circular, thus hampering the subsequent quantitative analysis. In contrast, with the use of the member of the instant invention, the operator is relieved of such skillful work. In the case of a rough application of the drop from the pipette, wiping the opening with a small piece of absorbent cotton impregnated with the sample fluid, or immersing the opening of the analysis member into the sample fluid, the fluid is always supplied to the porous spreading layer solely via the opening, leading invariably to a circular expansion pattern. In short, the analysis member of the instant invention simplifies application of the sample field.

(3) The existence of the waterproof cover layer has been proved to prevent rapid escape of water by evaporation. The sample fluid for analysis supplied through the small opening into the interior of the analysis sheet keeps the reagent layer in a moistened state for more than 20 to 30 minutes, which enables the aqueous phase reaction to proceed to completion.

(4) In the conventional analysis sheet, the spreading layer is the outermost layer and stands exposed, though it is essentially fragile and weak due to its high porosity. This fact necessarily requires careful handling of the sheet prior to and during analysis. On the other hand, the member of the instant invention, the major portion of the fragile spreading layer is protected by the waterproof layer, leading to a marked improvement in handling convenience.

(5) In case where a suitable backing or support is provided for the multilayer chemical analysis member of the instant invention, the reagent layer is sandwiched between the underlying backing and the outermost waterproof layer. In the conventional type of analysis sheet, the chemical reagent layer is covered only by the porous spreading layer, which means that the reagent layer is indirectly exposed to the ambient atmosphere at its one side. From this viewpoint, the member of the instant invention is evidently superior with regard to its storage stability.

(6) When the waterproof layer is made to reflect light by incorporating a suitable material such as a dye or pigment, the accuracy of the quantitative analysis performed to spectroscopically detect the degree of coloration of the chemical reagent layer can be improved by the effective use of reflected light from the waterproof layer.

While the invention has been described in detail and with reference to specific embodiments thereof, it will be apparent to one skilled in the art that various changes and modifications can be made therein without departing from the spirit and scope thereof.

What is claimed is:

1. A multilayer chemical analysis member comprising
    a waterproof layer having a thickness of 8 microns to 1 mm and provided with at least one opening having a size of about 30 microns to about 4 mm in diameter for application of a sample liquid to be tested;
    a porous spreading layer;
    a chemical reagent layer comprising a chemical reagent in a hydrophilic or hydrophobic medium, said reagent being capable of reacting with a test material in said sample liquid; and
    a support layer,
all of said layers being bonded together in a unified structure.

2. The multilayered chemical analysis member of claim 1, wherein said porous spreading layer is made of a fibrous material, a non-fibrous material, a micro-porous membrane filter or a polymer film filled with finely divided powder particles.

3. The multilayered chemical analysis member of claim 1, wherein said opening in said waterproof layer is a polygonal hole or a circular hole.

4. The multilayered chemical analysis member of claim 1, wherein said at least one opening comprises a plurality of small apertures each with a diameter of about 30 microns to about 0.5 mm and located within a circular area of about 1 mm to 5 mm in diamet.

5. The multilayered chemical analysis member of claim 1, wherein said waterproof layer is a waterproof film bonded to said porous spreading layer with an adhesive.

6. The multilayered chemical analysis member of claim 5, wherein said adhesive is a pressure sensitive adhesive.

7. The multilayered chemical analysis member of claim 1, wherein said waterproof layer is a waterproof adhesive film with an adhesive layer on one surface thereof.

8. The multilayered chemical analysis member of claim 7, wherein said adhesive layer is a layer of a pressure sensitive adhesive.

9. The multilayered chemical analysis member of claim 1, wherein said opening in said waterproof layer is an asterisk shaped cut, a cross cut or a linear slit.

* * * * *